United States Patent [19]

Arlt et al.

[11] Patent Number: 5,250,540
[45] Date of Patent: Oct. 5, 1993

[54] AMINOMETHYL-SUBSTITUTED 2,3-DIHYDROPYRANO[2,3-B]PYRIDINES AND THEIR USE IN MEDICAMENTS

[75] Inventors: Dieter Arlt, Köln; Hans-Georg Heine, Krefeld; Rudolf Schohe-Loop, Wuppertal; Thomas Glaser, Overath; Jean M. V. De Vry, Rösrath, all of Fed. Rep. of Germany

[73] Assignee: Bayer Aktiengesellschaft, Leverkusen, Fed. Rep. of Germany

[21] Appl. No.: 896,956

[22] Filed: Jun. 11, 1992

[30] Foreign Application Priority Data

Jun. 20, 1991 [DE] Fed. Rep. of Germany ....... 4120322

[51] Int. Cl.⁵ ............... C07D 491/052; A61K 31/435
[52] U.S. Cl. ............................. 514/302; 514/224.5; 544/33; 546/115; 546/116
[58] Field of Search ............... 546/115, 116; 544/33; 514/302, 224.5

[56] References Cited

U.S. PATENT DOCUMENTS 5,137,901  8/1992  Junge et al. ..................... 548/207

FOREIGN PATENT DOCUMENTS 0199400 10/1986 European Pat. Off. .
0236930  9/1987 European Pat. Off. .
0270947  6/1988 European Pat. Off. .
 352613  1/1990 European Pat. Off. .
0433149  6/1991 European Pat. Off. .

OTHER PUBLICATIONS

Chemical Society Reviews, vol. 18, 1979, pp. 563-580; C. W. Thornber: "Isosterism and Molecular Modification in Drug Design".
Chemical Abstracts, vol. 96, No. 25, Jun. 21, 1982, p. 740, paragraph No. 217799j, Columbus, Ohio, US: Dr. Pratap et al.: "Phenoxyalkylamines in semirigid conformation: synthesis and pharmacological activity of N1-(4'-chromanyl)-N4-arylpiperazines and N1-(2'-chromanylmethyl)-N4-arylpiperazines" & Indian J. Chem., Sect. B 1981, vol. 20 B, No. 12, pp. 1063-1067, Example III.
G. Burrell et al, "Variation in the Aromatic Ring of Cromakalim: . . . ", J. Med. Chem. 33 (11) pp. 3023-3027 (1990.
R. Sarges et al, "Spiro Hydantoin Aldose Reductase Inhibitors . . . ", J. Med. Chem. 33 (7), pp. 1859-1865 (1990).
Beilstein 2, p. 197, 201, 250, 278; (1920).
Beilstein 3, pp. 9 and 10; (1959).
Beilstein 21, pp. 461, 462 and 463, (1959).

Primary Examiner—Bernard Dentz
Attorney, Agent, or Firm—Sprung Horn Kramer & Woods

[57] ABSTRACT

Aminomethyl-substituted 2,3-dihydropyrano[2,3-b]pyridines can be prepared by alkylation of corresponding amines. The novel aminomethyl-substituted dihydropyrano[2,3-b]pyridines can be used as active ingredients in medicaments, in particular for the treatment of disorders of the central nervous system.

7 Claims, No Drawings

AMINOMETHYL-SUBSTITUTED 2,3-DIHYDROPYRANO[2,3-B]PYRIDINES AND THEIR USE IN MEDICAMENTS

The invention relates to aminomethyl-substituted 2,3-dihydropyrano[2,3-b]pyridines, process for their preparation and their use in medicaments, in particular in the case of disorders of the central nervous system.

It is already known that N-substituted aminomethyl-tetralin derivatives and their heterocyclic analogues possess a high affinity to receptors of the 5-HT$_1$ type and show activity on the cardiovascular and also the central nervous system [cf. European Patent 352,613 A2].

Moreover, 2H-pyrano[2,3-b]pyridin-4-ol derivatives having antihypertensive activity and the 4-carboxylic acid derivatives as aldose reductase inhibitors are described [cf. J. Med. Chem. 33 (11), 3023–3027; 33 (7), 1859–1865].

The invention relates to aminomethyl-substituted 2,3-dihydropyrano[2,3-b]pyridines of the general formula (I)

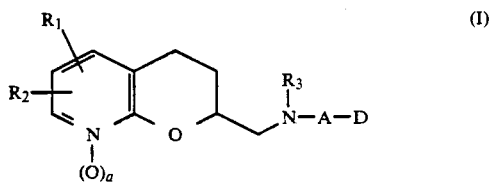

in which
R$^1$ and R$^2$ are identical or different and represent hydrogen, halogen, nitro, trifluoromethyl, hydroxyl or straight-chain or branched alkyl or alkoxy each having up to 8 carbon atoms,
a represents the number 0 or 1,
A represents straight-chain or branched alkylene or alkenylene each having up to 8 carbon atoms,
D represents cycloalkyl having 3 to 8 carbon atoms or aryl having 6 to 10 carbon atoms, or represents a group of the formula —NR$^4$R$^5$, —OR$^6$, —CO$_2$R$^7$ or —CO—NR$^8$R$^9$,
in which
R$^4$ and R$^5$ are identical or different and denote hydrogen, cycloalkyl having 3 to 8 carbon atoms, benzyl, straight-chain or branched alkyl having up to 8 carbon atoms or a group of the formula —CO—R$^{10}$ or —SO$_2$R$^{11}$,
in which
R$^{10}$ and R$^{11}$ are identical or different and denote straight-chain or branched alkyl having up to 8 carbon atoms or denote benzyl, aryl having 6 to 10 carbon atoms or a 5- to 7-membered unsaturated heterocycle having up to 4 hetero atoms selected from the group comprising S, N or O, each of which is optionally substituted by nitro, cyano, trifluoromethyl, halogen, amino, carboxyl, hydroxyl or by straight-chain or branched alkyl, alkoxy or alkoxycarbonyl each having up to 6 carbon atoms,
R$^4$ and R$^5$ together with the nitrogen atom form a radical of the formula

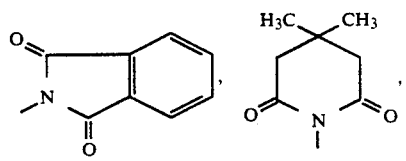

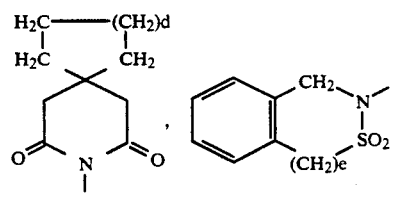

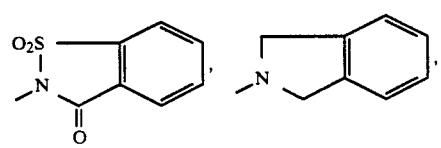

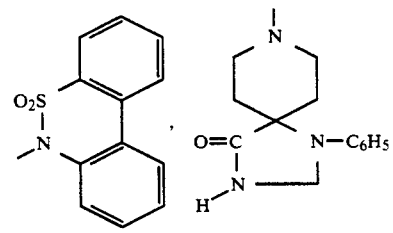

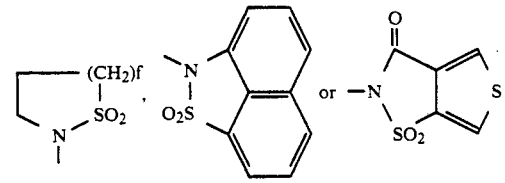

in which
d and f are identical or different and denote the number 1 or 2,
e denotes the number 0, 1 or 2,
R$^6$ denotes hydrogen, cycloalkyl having 3 to 8 carbon atoms, straight-chain or branched alkyl, alkylcarbonyl or carbamoyl each having up to 6 carbon atoms, or denotes benzyl, aryl having 6 to 10 carbon atoms or a 5-membered unsaturated heterocycle having up to 4 hetero atoms selected from the group comprising N, S or O, each of which is optionally substituted by nitro, cyano, trifluoromethyl, halogen, amino, carboxyl, hydroxyl or by straight-chain or branched alkyl, alkoxy or alkoxycarbonyl each having up to 6 carbon atoms,
R$^7$ denotes hydrogen, straight-chain or branched alkyl having up to 6 carbon atoms or benzyl,
R$^8$ and R$^9$ are identical or different and denote hydrogen, straight-chain or branched alkyl having up to 8 carbon atoms, benzyl or aryl having 6 to 10 carbon atoms,
R$^3$ represents hydrogen, straight-chain or branched alkyl having up to 8 carbon atoms or benzyl, or represents the —A—D group,
in which
A and D have the meanings given above, and their salts.

The compounds according to the invention can also be present in the form of their salts. In general salts with inorganic or organic acids may be mentioned here. Preference is given to physiologically acceptable salts.

The compounds according to the invention can exist in stereoisomeric forms, which either act like object and mirror image (enantiomers), or do not act like object and mirror image (diastereomers). The invention relates both to the antipodes as well as to the racemic forms and also the diastereomer mixtures. The racemic forms and also the diastereomers may be separated by a known method into the stereoisomerically uniform components [cf. E. L. Eliel, Stereochemistry of Carbon Compounds, McGraw Hill, 1962].

Physiologically acceptable salts of the aminomethyl-substituted 2,3-dihydropyrano[2,3-b]pyridines can be salts of the substances according to the invention with mineral acids, carboxylic acids or sulphonic acids. Particular preference is given for example to salts with hydrochloric acid, methanesulphonic acid, ethanesulphonic acid, toluenesulphonic acid, benzenesulphonic acid, naphthalenedisulphonic acid, acetic acid, propionic acid, lactic acid, oxalic acid, malonic acid, succinic acid, maleic acid, fumaric acid, maleic acid, tartaric acid, citric acid or benzoic acid.

Heterocycle in the context of the definition given above generally represents a 5- to 7-membered aromatic ring, which can contain oxygen, sulphur and/or nitrogen as hetero atoms and onto which a further aromatic ring can be condensed. Preference is given to 5- and 6-membered aromatic rings, which contain an oxygen, a sulphur and/or up to 2 nitrogen atoms and which are optionally condensed on to a benzo group. Particularly preferred heteroaryl radicals which may be mentioned are: thienyl, furyl, pyridyl, pyrimidyl, pyrazinyl, pyridazinyl, quinolyl, isoquinolyl, quinoxazolyl, quinolyl, thiazolyl, benzothiazolyl, isothiazolyl, oxazolyl, isoxazolyl, imidazolyl, benzimidazolyl, pyrazolyl and indolyl.

Preference is given to compounds of the general formula (I),
in which
$R^1$ and $R^2$ are identical or different and represent hydrogen, fluorine, chlorine, bromine, nitro, trifluoromethyl, hydroxyl or straight-chain or branched alkyl or alkoxy each having up to 6 carbon atoms,
a represents the number 0 or 1,
A represents straight-chain or branched alkylene or alkenylene each having up to 6 carbon atoms,
D represents cyclopropyl, cyclopentyl, cyclohexyl or phenyl, or represents a group of the formula $-NR^4R^5$, $-OR^6$, $-CO_2R^7$ or $-CO-NR^8R^9$,
in which
$R^4$ and $R^5$ are identical or different and denote hydrogen, cyclopropyl, cyclopentyl, cyclohexyl, benzyl, straight-chain or branched alkyl having up to 6 carbon atoms or a group of the formula $-CO-R^{10}$ or $-SO_2R^{11}$,
in which
$R^{10}$ and $R^{11}$ are identical or different and denote straight-chain or branched alkyl having up to 6 carbon atoms, or denote benzyl or phenyl, each of which is optionally substituted by nitro, cyano, trifluoromethyl, fluorine, chlorine, carboxyl, hydroxyl or by straight-chain or branched alkyl, alkoxy or alkoxycarbonyl each having up to 4 carbon atoms, $R^4$ and $R^5$ together with the nitrogen atom form a radical of the formula

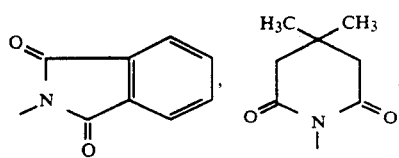

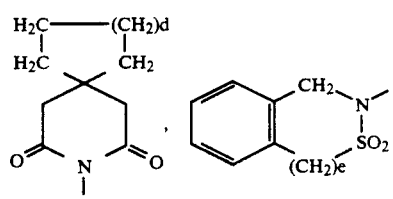

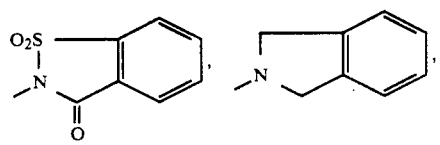

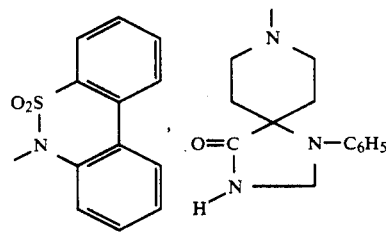

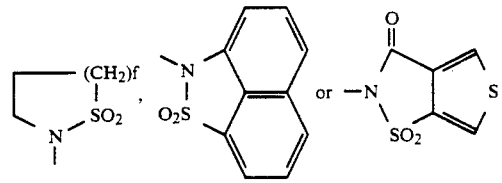

in which
d and f are identical or different and denote the number 1 or 2,
e denotes the number 0, 1 or 2,
$R^6$ denotes hydrogen, straight-chain or branched alkyl, alkylcarbonyl or carbamoyl each having up to 4 carbon atoms, or benzyl denotes or phenyl, each of which is optionally substituted by nitro, cyano, trifluoromethyl, halogen, amino, carboxyl, hydroxyl or straight-chain or branched alkyl, alkoxy or alkoxycarbonyl each having up to 6 carbon atoms,
$R^7$ denotes hydrogen, straight-chain or branched alkyl having up to 4 carbon atoms or benzyl,
$R^8$ and $R^9$ are identical or different and denote hydrogen, straight-chain or branched alkyl having up to 6 carbon atoms, benzyl or phenyl,
$R^3$ represents hydrogen, straight-chain or branched alkyl having up to 6 carbon atoms or benzyl, or represents the $-A-D$ group,
in which
A and D have the meanings given above, and their salts.

Particular preference is given to compounds of the general formula (I), in which $R^1$ and $R^2$ are identical or different and represent hydrogen, fluorine, chlorine, trifluoromethyl, hydroxyl or straight-chain or branched alkyl or alkoxy each having up to 4 carbon atoms, a represents the number 0 or 1, A represents straight-chain or branched alkylene or alkenylene each having up to 4 carbon atoms, D represents cyclopropyl, cyclopentyl, cyclohexyl, hydroxyl or phenyl, or represents a group of the formula $-NR^4R^5$, in which $R^4$ and $R^5$ are identical or different and denote hydrogen, cyclopropyl, cyclopentyl, cyclohexyl, benzyl or straight-chain or branched alkyl having up to 4 carbon atoms, or $R^4$ and $R^5$ together with the nitrogen atom form a radical of the formula

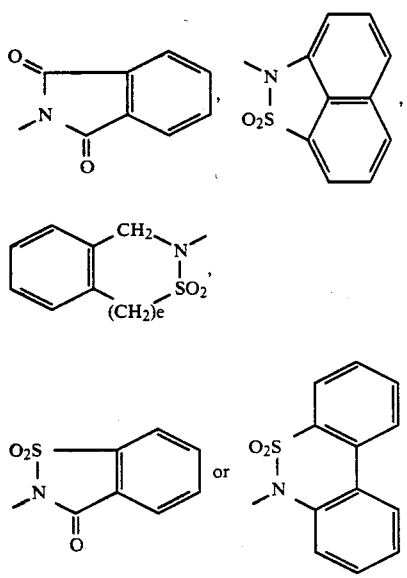

in which e denotes the number 0 or 1, $R^3$ represents hydrogen, straight-chain or branched alkyl having up to 4 carbon atoms or benzyl, represents the —A—D group, in which A and D have the meanings given above, and their salts In addition, a process for the preparation of the compounds according to the invention of the general formula (I) has been found, characterised in that amines of the general formula (II)

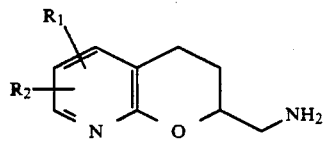

(II)

in which $R^1$ and $R^2$ have the meanings given above, are reacted with compounds of the general formula (III)

 L—A—D (III)

in which

A and D have the meanings given above and

L represents a typical leaving group, such as for example bromine, chlorine, iodine, tosyl or mesyl, preferably bromine, in inert solvents, optionally in the presence of a base and a reaction accelerator, and for the case that $R^3$ does not represent hydrogen, there is a subsequent alkylation, and for the case of the 2,3-dihydropyrano[2,3-b]pyridine N-oxides (a=1), there is a subsequent oxidation, in each case according to conventional methods.

The solvent used can be water or the conventional organic solvents which do not alter under the reaction conditions. Preference is given in this context to alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoric triamide, or dimethyl sulphoxide, acetonitrile, ethyl acetate, or halogenated hydrocarbons such as methylene chloride, chloroform or carbon tetrachloride, or pyridine, picoline or N-methylpiperidine. Mixtures of the solvents mentioned can likewise be used. Preference is given to dimethylformamide.

Suitable bases are the conventional inorganic or organic bases. Preference is given in this context to alkali metal hydroxides such as for example sodium hydroxide or potassium hydroxide, or alkali metal carbonates such as sodium carbonate or potassium carbonate, or alkali metal alcoholates such as for example sodium methanolate or potassium methanolate, or sodium ethanolate or potassium ethanolate, or organic amines such as triethylamine, picoline or N-methylpiperidine, or amides such as sodium amide or lithium diisopropylamide, or organometallic compounds such as butyllithium or phenyllithium. Preference is given to triethylamine.

The base is used here in a quantity of from 1 to 5, preferably from 1 to 2 mol, relative to 1 mol of the compounds of the general formula (III). The compounds of the general formula (III) are preferably used in an up to 3-fold, preferably in an up to 1.5-fold excess over the compounds of the formula (II).

The reaction accelerators used are generally alkali metal iodides, preferably sodium iodide or potassium iodide, in a quantity of 0.01 mol to 0.5 mol, preferably 0.01 mol to 0.1 mol, relative to 1 mol of the compounds of the general formula (III).

The reaction is generally carried out in a temperature range from 0° C. to +150° C., preferably in a range from room temperature to +80° C.

The reaction mixture is generally carried out at standard pressure. However, it is equally possible to carry out the reaction at elevated or reduced pressure (for example 0.5 to 3 bar).

The alkylation is generally carried out in one of the solvents listed above, preferably in dimethylformamide, in a temperature range from 0° C. to +158° C., preferably from room temperature to +100° C.

The alkylating agents used in the process can be for example $(C_1-C_8)$-alkyl halides, sulphonic esters or substituted or unsubstituted $(C_1-C_6)$-dialkyl sulphates or $(_6-C_{10})$-diaryl sulphates, preferably methyliodide, p-toluenesulphonic esters or dimethyl sulphate.

The oxidation to the N-oxide is generally carried out in one of the solvents listed above, preferably in methylene chloride using oxidation agents such as for example metachloroperbenzoic acid, hydrogen peroxide or peracetic acid, preferably using metachloroperbenzoic acid in a temperature range from 0° C. to 120° C., preferably from 20° C. to 80° C.

Both the oxidation and the alkylation can generally be carried out at standard pressure. However, it is equally possible to carry out the reaction at elevated or reduced pressure (for example 0.5 to 3 bar).

The compounds of the general formula (II) are novel and can be prepared by reacting compounds of the formula (IV)

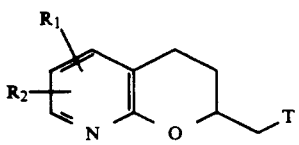
(IV)

in which
$R^1$ and $R^2$ have the meanings given above, and
T represents halogen, preferably bromine and/or chlorine,
optionally as a mixture (T—Br, T—Cl), firstly with potassium phthalimide in inert solvents and under a protective gas atmosphere to give the compounds of the general formula (V)

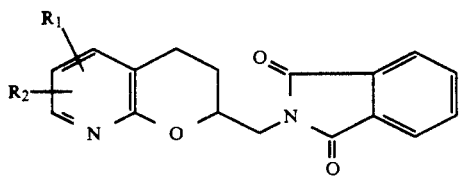
(V)

in which
$R^1$ and $R^2$ have the meanings given above,
and, in a second step, liberating the amine function by reaction with 2-amino-ethanol or hydrazine hydrate.

Suitable solvents for the reaction with potassium phthalimide/2-aminoethanol are the abovementioned solvents, preferably dimethylformamide, and toluene, 2-aminoethanol itself optionally through acting as solvent in the second step use in a large excess.

The reactions proceed in a temperature range from +50° C. to +150° C., preferably from +60° C. to +120° C. and atmospheric pressure.

The compounds of the general formula (III) are known [cf. Beilstein 2, 197, 201, 250, 278; 3. 9, 10; 21. 401, 462, 463].

The compounds of the general formula (V) are novel and can be prepared by the process described above.

The compounds of the general formula (IV) are likewise novel and can be prepared by first converting compounds of the general formula (VI)

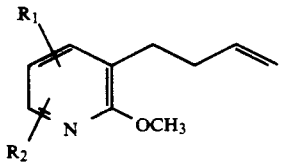
(VI)

in which
$R^1$ and $R^2$ have the meanings given above,
by bromination, preferably using elemental bromine, in one of the solvents listed above, preferably methylene chloride, into compounds of the general formula (VII)

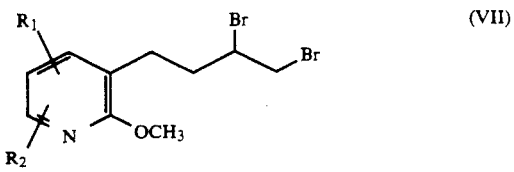
(VII)

in which
$R^1$ and $R^2$ have the meanings given above,
and subsequently closing the ring in a 2-step process by reaction with dilute hydrochloric acid and sodium carbonate/sodium hydrogen carbonate solution to give the 6-membered heterocycle.

The compounds of the general formula (VII) are likewise novel.

The compounds of the general formula (VI) are novel and can be prepared by chlorinating compounds of the general formula (VIII)

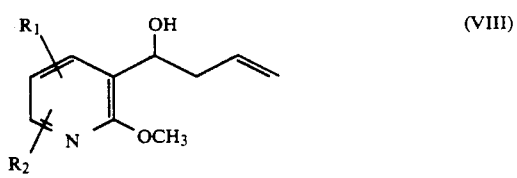
(VIII)

in which
$R^1$ and $R^2$ have the meanings given above,
by reaction with the conventional chlorination agents, preferably thionyl chloride in one of the solvents listed above, preferably dichloromethane, and reducing the product in a following step, for example using copper-activated zinc, in one of the solvents listed above, preferably methanol, or using tributyltin hydride in hydrocarbons, in this case preferably using toluene.

The above-described reactions are generally carried out in a temperature range from 0° C. to +120° C., preferably from +20° C. to +100° C. and atmospheric pressure.

The compounds of the general formula (VIII) are likewise novel and can for example be prepared by reacting either the 2-methoxypyridine-3-carbaldehyde ($R^1/R^2$=H) disclosed in the literature, or its substituted derivatives ($R^1/R^2\neq$H) with allyl bromide and aluminium in the presence of mercury(II) chloride in one of the above-mentioned ethers, preferably tetrahydrofuran.

The reaction is generally carried out in a temperature range from −60° C. to +50° C., preferably from −60° C. to +25° C. and atmospheric pressure.

The substances according to the invention surprisingly show an advantageous activity on the central nervous system and can be used for therapeutic treatment of humans and animals. Compared to the already known structurally related compounds they are distinguished by a higher selectivity for the 5-HT$_{1A}$ receptor, by some serotonin antagonistic activity and fewer side effects.

They have agonistic, partially agonistic or antagonistic activities on the serotonin receptor. In comparison to the structurally related known compounds, they surprisingly have a wider therapeutic range.

The high-affinity ligands for the serotonin-1-receptor described in the present invention are thus active ingredients for the control of disorders characterised by disturbances of the serotoninergic system, in particular with involvement of receptors having high affinity for 5-hydroxytryptamine (serotonin) (5-HT$_1$-type). They are thus suitable for treatment of disorders of the central nervous system such as conditions of anxiety, tension and depression, central nervous system-dependent sexual dysfunctions and sleep disturbances and food intake disturbances. Furthermore, they are suitable for the elimination of cognitive deficits, for the improvement of learning performance and memory performance and for treatment of Alzheimer's disease.

Furthermore, these active ingredients are also suitable for modulation of the cardiovascular system. They also intervene in the regulation of the cerebral blood supply and are thus effective agents for the control of migraine.

They are also suitable for the prophylaxis and control of the consequences of cerebral infarctions such as stroke, acute cranio-cerebral trauma, cerebral ischaemia and their resultant effects. The compounds according to the invention can likewise be used for the control of disorders of the intestinal tract, which are characterised by disturbandes of the serotoninergic system and also by disturbances of the carbohydrate balance.

Affinity to the 5-HT$_1$-receptor

In Table 1 the high affinity of the compounds according to the invention for 5-hydroxytryptamine receptors of subtype 1 is exemplified. The values given relate to data obtained from receptor binding studies using preparations of calf hippocampus membranes. The radioactively labelled ligand used for this was $^3$H-serotonin.

TABLE 1

| Compound of the Example | K$_i$ (nmol/l) |
|---|---|
| 4 | 1.0 |

The present invention also relates to pharmaceutical preparations, which, in addition to inert, non-toxic, pharmaceutically acceptable adjuncts and excipients, contain one or more compounds of the general formula (I), or which are composed of one or more active ingredients of the formula (I), and also to processes for the production of these preparations.

The active ingredients of the formula (I) are present in these preparations in a concentration of from 0.1 to 99.5% by weight, preferably from 0.5 to 95% by weight of the total mixture.

In addition to the active ingredients of the formula (I) the pharmaceutical preparations can also contain other pharmaceutical active ingredients.

The above-described pharmaceutical preparations can be prepared in a conventional manner according to known methods, for example using the adjunct(s) or excipient(s).

It has generally proved advantageous to administer the active ingredient(s) of the formula (I) in total quantities of approximately 0.01 to approximately 100 mg/kg, preferably in total quantities of approximately 1 mg/kg to 50 mg/kg of body weight per 24 hours, optionally in the form of a plurality of individual doses, to achieve the desired result.

However, it can be advantageous, if required, to deviate from the quantities mentioned, particularly depending on the type and body weight of the subject, on the individual reaction to the medicament, the type and severity of the disorder, the type of the preparation and application, and also the point in time and/or interval at which the administration is carried out.

STARTING COMPOUNDS

EXAMPLE I 3-(1-Hydroxy-but-3-en-1-yl)-2-methoxypyridine

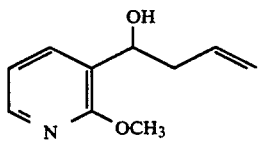

29.9 g (1.1 g-atom) of aluminium flakes and 100 mg of mercury(II) chloride are suspended in 300 ml of anhydrous tetrahydrofuran under argon. The mixture is heated to 40° C. and 1-2 ml of 214.0 g (1.77 mol) of allyl bromide in 250 ml of anhydrous tetrahydrofuran are slowly added dropwise. The temperature during this rises to approximately 50° C. The allyl bromide solution is then added dropwise with stirring at such a rate that the temperature of the solution does not exceed 50° C. The solution is subsequently stirred for 1 hour at 60° C., and cooled to −60° C. and 112.4 g (0.765 mol) of 2-methoxypyridine-3-carbaldehyde in 250 ml of anhydrous tetrahydrofuran are added dropwise at this temperature. The mixture is then stirred for 1 hour at 0° C. and for 2 hours at 20° C. Subsequently, 500 ml of saturated ammonium chloride solution are added dropwise with cooling, the mixture is stirred for 0.5 hours, filtered and the filtrate is concentrated in vacuo. The residue is taken up in ethyl acetate, washed with water and dried over sodium sulphate. 136.1 g of a light yellow oil is obtained which is fractionally distilled.

Yield: 110.9 g (81% of theory)
B.P. 91°–100° C./0.5 mmHg.

EXAMPLE II 3-(1-Chloro-but-3-en-1-yl)-2-methoxypyridine

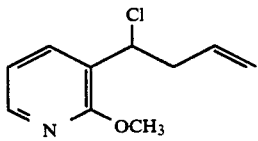

56.5 g (0.32 mol) of the compound from Example I are stirred in 400 ml of anhydrous dichloromethane containing 277 ml (3.8 mol) of thionyl chloride overnight at 20°–30° C. Subsequently, dichloromethane and unreacted thionyl chloride are removed in a water pump vacuum at 20°–30° C. The residue is partitioned between dichloromethane and aqueous saturated sodium bicarbonate solution. The organic phase is separated off, dried and evaporated in vacuo. 59.3 g of the crude title compound are obtained as an oil.

Yield: 94% of theory

EXAMPLE III 3-(But-3-en-1-yl)-2-methoxypyridine

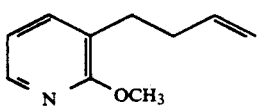

A total of 71.4 g of zinc (copper-activated) are added to 118.5 g (0.54 mol) of the compound from Example II in 1000 ml of anhydrous methanol, and the mixture is refluxed for 2 hours. The precipitate is filtered off, and the filtrate is subsequently evaporated in vacuo. Fractional distillation of the residue produces 20.0 g of the title compound having b.p. 96° C./20 mmHg.

Yield: 23% of theory

EXAMPLE IV 3-(3,4-dibromo-but-1-yl)-2-methoxypyridine

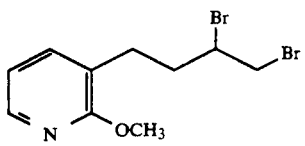

14.4 g (88 mmol) of bromine in 30 ml of anhydrous dichloromethane are added dropwise at 20°–30° C. to a solution of 14.0 g (88 mmol) of the compound from Example III in 70 ml of anhydrous dichloromethane with stirring. After 15 minutes cold saturated sodium bicarbonate solution is added to the reaction mixture, a few ml of sodium sulphite solution are added and the phases are separated. The dichloromethane phase is dried and evaporated in vacuo. 28.1 g of the crude title compound are obtained as an oil.

Yield: 100% of theory

EXAMPLE V AND EXAMPLE VI (2-Bromo-methyl)-2,3-dihydropyrano(2,3-b)pyridine

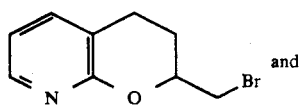

and (2-chloro-methyl)-2,3-dihydropyrano(2,3-b)pyridine (VI)

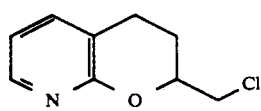

28.1 g (88 mmol) of the crude compound from Example IV are refluxed in 212 ml of 5% strength aqueous hydrochloric acid under nitrogen and with stirring for 4.5 hours. After cooling to 20° C. the reaction mixture is extracted with n-hexane. The aqueous phase is then made alkaline by addition of soda solution and extracted with dichloromethane. Evaporation of this phase in vacuo produces 15.0 g of crystalline product, which contains the title compounds in the ratio 12:5 (V/VI).

Yield: approximately 79% of theory.

EXAMPLE VII

2-Phthalimidomethyl-2,3-dihydropyrano(2,3-b)pyridine

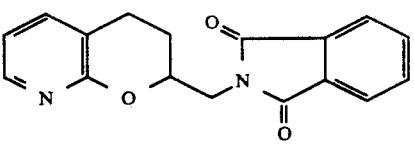

15.0 g (70 mmol) of a mixture of the compounds from Example V and VI (ratio 12:5) are heated at 100° C. with 16.0 g (86 mmol) of potassium phthalimide in 150 ml of dimethylformamide under nitrogen with stirring for 20 hours. Dimethylformamide is then distilled off in vacuo and the residue is partitioned between dichloromethane and water. 24.0 g of crystals having a melting range of 152°–158° C. are obtained.

NMR (CDCl$_3$): 1.70–2.00 (m, 1H); 2.00–2.20 (m, 1H) 2.80–2.90 (m, 2H); 3.80–3.95 and 4.10–4.25 (AB system, 2H); 4.50–4.65 (m, 1H); 6.75–6.90 (m, 1H); 7.30–7.40 (m, 1H); 7.65–7.80 (m, 2H); 7.80–7.95 (m, 2H) and 8.00–8.10 (m, 1H) ppm.

Yield: approximately 100% of theory

EXAMPLE VIII

2-Aminomethyl-2,3-dihydropyrano(2,3-b)-pyridine

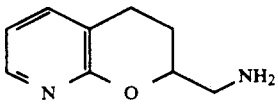

3.2 g (11 mmol) of the compound from Example VII and 9.2 g (150 mmol) of 2-aminoethanol are heated under nitrogen to 80° C. After 5 minutes the mixture is cooled, and the reaction mixture is partitioned between 70 ml of toluene and 92 ml of 5% strength NaCl solution. The phases are separated, and the aqueous phase is extracted with dichloromethane. The combined organic phases are dried and evaporated in vacuo. 1.7 g of the title compound are obtained as a light yellow oil.

Yield: 94% of theory.

NMR (CDCl$_3$): 1.73–1.85 (m, 1H); 1.93–2.00 (m, 3H, 2H exchange on addition of D$_2$O); 2.74–2.95 (m) and 2.96 (quasi d, 4H); 4.09–4.18 (m, 1H); 6.81–6.86 (m, 1H); 7.35–7.37 (m, 1H) and 8.04–8.05 (m, 1H) ppm.

PREPARATION EXAMPLES

EXAMPLE 1 AND EXAMPLE 2

2-N-Bis-(4-butylsaccharinyl)-aminomethyl-2,3-dihydropyrano[2,3-b]pyridine (I)

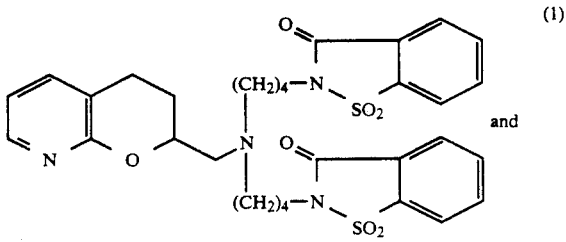

2-N-(4-butylsaccharinyl)-aminomethyl-2,3-dihydropyrano[2,3-b]pyridine (2)

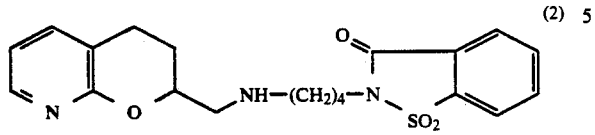

2.1.g (11 mmol) of the compound from Example VIII, 3.5 g (11 mmol) of 4-bromobutylsaccharin, 1.1 g (11 mmol) of triethylamine and 10 mg of sodium iodide are stirred in 10 ml of dimethylformamide for 9 hours at 60° C. (complete conversion) under argon. Dimethylformamide is distilled off at 0.01 mmHg and 40° C. The residue is partitioned between water and dichloromethane and the phases are separated. The organic phase is made alkaline with 0.1N NaOH, washed with water, then dried over sodium sulphate and evaporated. 4.0 g of a light yellow oil are obtained, which are chromatographed on 200 g of silica gel using toluene/ethyl acetate (gradient). 0.7 g of 2-N-bis-(4-butylsaccharinyl)-aminomethyl-2,3-dihydropyrano[2,3-b]pyridine (1) is obtained.

Yield: 10% of theory
NMR (CDCl$_3$) 1.54–1.86 (m, 9H); 2.19–2.34 (m, 1H); 2.54–2.86 (m, 8H); 3.76–3.82 (m, 4H); 4.20–4.30 (m, 1H); 6.77–6.82 (m, 1H); 7.34–7.37 (m, 1H); 7.78–7.91 (m, 6H); and 8.01–8.04 (m, 3H) ppm.

The aqueous phase (pH 5.5) is made alkaline with 0.1N NaOH and/is shaken with dichloromethane. The dichloromethane extracts are subsequently washed with water, dried over sodium sulphate and evaporated. The residue (1.2 g) is chromatographed on 60 g of silica gel using toluene/methyl acetate 1:1, and 0.2 g of 2-N-(4-butylsaccharinyl)-aminomethyl-2,3-dihydropyrano[2,3-b]pyridine (2) is obtained.

Yield: 5% of theory.
NMR (CDCl$_3$) 1.62–2.05 (m, 6H); 2.74–3.40 (m, 7H); 3.76–3.82 (m, 2H); 4.32–4.00 (m, 1H); 6.80–6.85 (m, 1H); 7.36–7.39 (m, 1H); 7.79–7.93 (m, 3H) and 8.02–8.05 (m, 2H) ppm.

EXAMPLE 3

2-N-Bis-(4-butylsaccharinyl)-aminomethyl-2,3-dihydropyrano[2,3-b]pyridine HCl salt

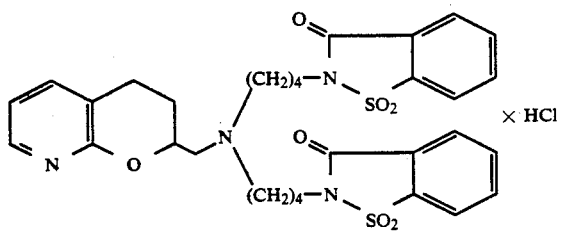

0.7 g of the compound from Example 1 is dissolved in 100 ml of diethyl ether and made weakly acid (pH 4–5) using 1M etherial hydrochloric acid. 0.5 g of the title compound is obtained as an amorphous salt.

| $C_{31}H_{34}N_4O_7S_2$ × 2HCl | | |
|---|---|---|
| Calculated: C 52.32 | H 5.10 | N 7.87 |
| Found: C 53.1–53.5 | H 5.01–5.02 | N 7.88–7.97 |

EXAMPLE 4

2-N-(4-Butylsaccharinyl)-aminomethyl-2,3-dihydropyrano2,3-b]pyridine HCl salt

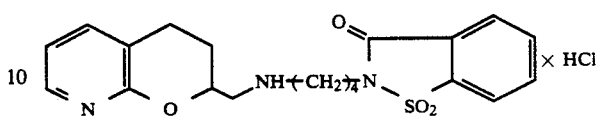

0.2 g of the compound from Example 2 is dissolved in 50 ml of diethyl ether and made weakly acid (pH 4–5) using 1M etherial hydrochloric acid. The hygroscopic precipitate is filtered off with suction and washed with diethyl ether. 0.1 g of a crystalline salt of the title compound is obtained having a melting range of 42°–50° C. NMR (CDCl$_3$/DMSO-d$_6$): characteristic signals at 4.6–4.8 (broad m, 2–3H); 7.0–7.1 (m, 1H), 7.7–7.8 (m, 1H); 7.9–8.1 (m, 4H); 8.2–8.2 (m, 1H) and 9.3 and 9.5 (m, each 2H) ppm.

We claim:
1. An aminomethyl-substituted 2,3-dihydropyrano[2,3-b]pyridine compound of the formula (I):

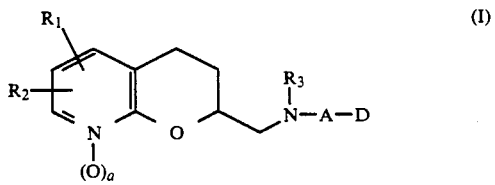

in which
R$_1$ and R$_2$ are identical or different and represent hydrogen, halogen, nitro, trifluoromethyl, hydroxyl or straight-chain or branched alkyl or alkoxy each having up to 8 carbon atoms;

R$_3$ represents hydrogen, straight-chain or branched alkyl having up to 8 carbon atoms or benzyl, or represents the —A—D group;

a represents the number 0 to 1;

A represents straight-chain or branched alkylene or alkenylene each having up to 8 carbon atoms; and D represents:

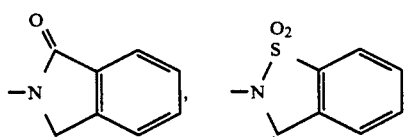

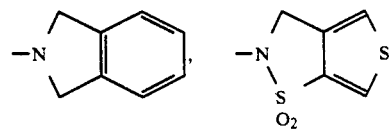

-continued

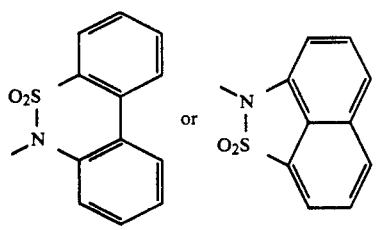

or a salt of said compound.

2. A compound according to claim 1, wherein $R_1$ and $R_2$ are identical or different and represent hydrogen, fluorine, chlorine, bromine, nitro, trifluoromethyl, hydroxyl or straight-chain or branched alkyl or alkoxy each having up to 6 carbon atoms;

$R_3$ represents hydrogen, straight-chain or branched alkyl having up to 6 carbon atoms or benzyl, or represents the —A—D group; and A represents straight-chain or branched alkylene or alkenylene each having up to 6 carbon atoms;

or a salt of said compound.

3. A compound according to claim 1, wherein $R_1$ and $R_2$ are identical or different and represent hydrogen, fluorine, chlorine, trifluoromethyl, hydroxyl or straight-chain or branched alkyl or alkoxy each having up to 4 carbon atoms;

$R_3$ represents hydrogen, straight-chain or branched alkyl having up to 4 carbon atoms or benzyl, or represents the —A—D group;

A represents straight-chain or branched alkylene or alkenylene each having up to 4 carbon atoms; and D represents

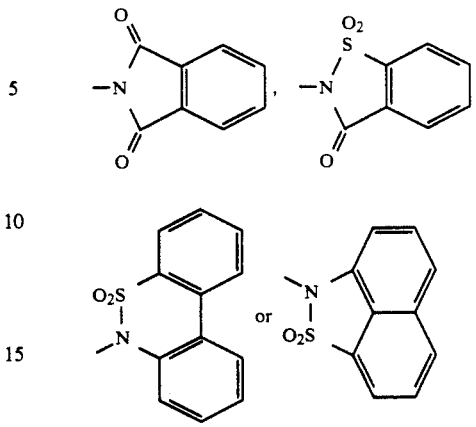

or a salt of said compound.

4. A compound according to claim 1, wherein such compound is 2-N-(4-butylsaccharinyl)aminomethyl-2,3-dihydropyrano[2,3-b]pyridine of the formula

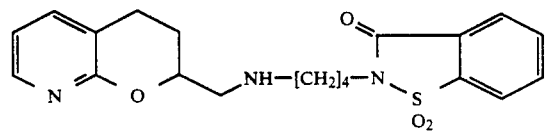

or a salt thereof.

5. A composition for the treatment of disorders, characterized by disturbances of the serotoninergic system comprising an amount effective therefore of a compound or salt thereof according to claim 1 and a pharmacologically acceptable diluent.

6. The method of treating disorders characterized by disturbances of the serotininergic system in a patient in need thereof which comprises administering to such patient an amount effective therefore of a compound or salt thereof according to claim 1.

7. The method of treating disorders characterized by disturbances of the serotininergic system in a patient in need thereof which comprises administering to such patient an amount effective therefore of a compound or salt thereof, wherein such compound is 2-N-(4-butylsaccharinyl)aminomethyl-2,3-dihydropyrano[2,3-b]pyridine.

* * * * *

UNITED STATES PATENT AND TRADEMARK OFFICE
CERTIFICATE OF CORRECTION

PATENT NO : 5,250,540
DATED : October 5, 1993
INVENTOR(S): Dieter ARLT, et al.

It is certified that error appears in the above-identified patent and that said Letters Patent is hereby corrected as shown below:

Column 14, line 49, cancel "to" and substitute --or--

Column 14, line 65, cancel " 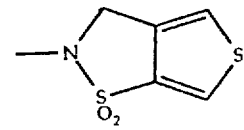 "

and substitute --  --

Signed and Sealed this

Fourteenth Day of December, 1999

Attest:

Q. TODD DICKINSON

Attesting Officer

Acting Commissioner of Patents and Trademarks